United States Patent [19]

Freeman

[11] Patent Number: 4,560,578
[45] Date of Patent: Dec. 24, 1985

[54] METHOD AND APPARATUS FOR SURFACE REPLICATION ON A COATED SHEET MATERIAL

[75] Inventor: Eben W. Freeman, Portland, Me.

[73] Assignee: Scott Paper Company, Philadelphia, Pa.

[21] Appl. No.: 627,388

[22] Filed: Jul. 3, 1984

Related U.S. Application Data

[63] Continuation-in-part of Ser. No. 320,771, Nov. 12, 1981, abandoned.

[51] Int. Cl.$^4$ .................... B05D 3/06; B05D 5/00; B05C 11/02
[52] U.S. Cl. .................................. 427/44; 118/68; 118/102; 427/278
[58] Field of Search ............... 427/278, 44, 276, 264; 118/44, 102, 68

[56] References Cited

U.S. PATENT DOCUMENTS

| | | | |
|---|---|---|---|
| 344,086 | 6/1886 | Derick | 427/276 X |
| 832,423 | 10/1906 | Rodriguez | 29/121.2 |
| 1,611,204 | 12/1926 | Quaglia | 29/121.6 X |
| 4,289,821 | 9/1981 | Gray et al. | 428/172 |

*Primary Examiner*—Evan K. Lawrence

[57] ABSTRACT

Disclosed is a method and apparatus for providing surface replication in a coating on a sheet material. The method comprises the steps of:

A. applying a flowable coating of a settable composition or material to one side of a web of sheet material;

B. pressing the coated side of the sheet material against a replicative surface having a desired contoured surface effect of peaks and valleys to cause the surface of the coating to conform to the replicative surface;

C. setting the coating to a nonflowable state at least sufficiently to enable it to be removed from the replicative surface securely attached to the sheet material and with the replicated surface effect in the coating being maintained; and D. stripping the sheet material from the replicative surface with the at least partially set coating adhered to the sheet material, characterized by the replicative surface comprising a cylinder having the desired surface effect in the central portion of its outer cylindrical surface and extending laterally less than the width of the sheet material on both sides and being bordered on both sides by cylindrical bands of a smooth surface extending beyond the width of the sheet material and having a diameter no less than the diameter of the valleys of the contoured surface effect area, and the coating extending laterally into the area of the smooth surface bands, whereby the set coating material fills all of the desired surface effect area and is stripped cleanly from the replicative surface and the smooth surface bands.

9 Claims, 4 Drawing Figures

METHOD AND APPARATUS FOR SURFACE REPLICATION ON A COATED SHEET MATERIAL

RELATED APPLICATION

This application is a continuation-in-part of application Ser. No. 320,771, filed Nov. 12, 1981, abandoned.

TECHNICAL FIELD

The present invention relates to apparatus and method for providing a desired surface effect in coatings on paper and other sheet materials.

BACKGROUND ART

Although the present invention relates to coated sheet materials in general, its preferred application is with release sheets, and for convenience, the invention will be described as it relates to release sheets.

A number of processes exist in which a plastic film or sheet is formed on or against a release sheet and then separated from the release sheet after taking steps, such as cooling or curing, to set the film or sheet. Curing, where necessary, may be accomplished by heat, by peroxide catalyst, or by U.V. radiation or by electron beam radiation. The release sheet provides a surface from which the set plastic material can be readily separated and imparts to the surface of the plastic material the quality of finish of the release surface. For example, a desired textured surface can be provided on the surface of the plastic material by forming on or against a release sheet having the mirror image of the desired textured surface.

One example of such forming processes is "casting", wherein a resinous material, such as polyvinyl chloride or polyurethane resin, in a flowable state is desposited or "cast" onto the release sheet surface, heated, cured and cooled to consolidate the resinous material into a continuous self-supporting film, and stripped from the support. The release sheet is normally provided with a desired surface effect, such as high gloss, texturing or an embossed configuration, and the surface effect is replicated on the cast film.

Another example of such forming processes is "panel pressing" of decorative plastic laminates, which can be either of the high pressure or low pressure type. In high pressure panel pressing, decorative laminates are conventionally prepared by assembling in a stacked relationship a plurality of core sheets, each of which is a web of paper impregnated with a resinous material, such as phenolic resin. Immediately positioned above the core sheet assembly is a decorative sheet, which is a resin saturated sheet having a solid color or a suitable design thereon. Superimposed above the decorative sheet is generally an overlay sheet, which is a thin sheet of fine paper impregnated with a noble thermosetting resin, such as a melamine formaldehyde resin or an unsaturated polyester resin and the like (and is generally the same resin used to impregnate the decorative sheet). The entire assembly of core sheets, decorative sheets, and overlay sheet is placed between platens in a press and consolidated by application of heat and pressure. Generally, a release sheet having the desired surface effect to be reproduced in the surface of the overlay sheet is placed against the overlay sheet during pressing. High pressure laminates after being consolidated are usually further glued to a structural substrate, such as particle board or plywood. Low pressure panel pressed decorative laminates are made in a similar manner to high pressure laminates, but generally involve lamination of the decorative sheet directly to particle board or other structural substrate.

Release sheets are typically made by coating, treating, or impregnating a paper sheet or other substrate with a release coating of such materials as polymethylpentene, polypropylene, polyfluorocarbons, silicone oil, thermoset silicone resins, and other conventional release agents. Surface effects on the release sheet are conventionally provided by any one of a number of techniques. The release coating can be dried to a smooth surface gloss, or surface effects such as texturing or embossing can be provided in the coating by mechanical means, applied either to the surface of the paper before coating or to the paper after the coating is applied.

A superior technique for producing surface effects in a release coating, or any other coating, is disclosed in U.S. Pat. No. 4,289,821 issued to Gray, et al. (which is herein incorporated by reference). In that patent, one method disclosed comprises applying a coating of an electron beam radiation curable composition or material to one side of a web of paper, pressing the coated side of the paper against a replicative surface having a desired contoured surface effect to cause the coating to conform to the replicative surface, irradiating the coating with electron beam radiation at least sufficiently to enable it to be removed from the replicative surface securely attached to the paper and with the replicated surface effect in the coating being maintained, and stripped the paper from the replicative surface with the cured coating adhered to the paper.

The replicative surface is preferably a metal roll with a texture or embossure engraved in its surface. One of the most important advantages of the technique is that the texture, embossure or other finish of the replicative surface is essentially one hundred percent reproduced in the cured coating. This achievement cannot be provided by any prior art technique, and it enables replication in the release paper of very fine patterns, such as wood grain and leather grain.

A disadvantage to the Gray, et al. process as disclosed is that the replicative surface pattern of the conventional engraved rolls extends from edge to edge across the width of the metal roll. In order to have a clean operation, coating is prevented from flowing over the edges of the roll by running a web of paper of less width than the roll and the coating is applied to the web so that it stays within the width of the web. Coating along the sides of the web fail to fill the cells of the engraved roll in this area and is not in continuous contact with the paper. As a result cured coating is not removed from the cells at the sides when the paper is stripped, thereby accumulating in these cells and producing an unstable condition of sticking between the web and the engraved roll at the sides. In addition, the build up of the coating continues until it holds the press roll too far away from the replicative roll to adequately provide the pressing step. This condition must be corrected frequently by shutting down the equipment and cleaning the roll.

The same disadvantage to the Gray, et al. process will exist with any similar replication process in which a flowable coating on a sheet material is set against a replication surface having a contoured surface effect (any three-dimensional surface effect having a pattern with depth). The problem is not just limited to release coatings or to electron beam curable coatings. The problem also exists if the coating is applied directly to the replicative surface rather than the paper. The present invention solves the problem in all of these cases.

SUMMARY OF THE INVENTION

The present invention is a method of providing surface replication in a coating on a sheet material, comprising the steps of:

A. applying a flowable coating of a settable composition or material to one side of a web of sheet material;
B. pressing the coated side of the sheet material against a replicative surface having a desired contoured surface effect of peaks and valleys to cause the surface of the coating to conform to the replicative surface;
C. setting the coating to a nonflowable state at least sufficiently to enable it to be removed from the replicative surface securely attached to the sheet material and with the replicated surface effect in the coating being maintained; and
D. stripping the sheet material from the replicative surface with the at least partially set coating adhered to the sheet material, characterized by the replicative surface comprising a cylinder having the desired surface effect in the central portion of its outer cylindrical surface, said surface effect extending laterally less than the width of the sheet material on both sides and being bordered on both sides by cylindrical bands of a smooth surface extending beyond the width of the sheet material and having a diameter no less than the diameter of the valleys of the contoured surface effect area, and the coating extending laterally into the area of the smooth surface bands, whereby the set coating material fills all of the desired surface effect area and is stripped cleanly from the replicative surface and the smooth surface bands.

The present invention is also an apparatus for providing surface replication in a coating on a sheet material, comprising:

A. a replicative surface having a desired contoured surface effect of peaks and valleys and being provided by a cylindrical surface mounted for revolution;
B. coating means for applying a coating of a settable composition or material directly to one side of the sheet material;
C. pressing means for pressing the coated side of the sheet material against the replicative surface to cause the surface of the coating opposite the sheet material to conform to the replicative surface;
D. means for setting the coating to a nonflowable state at least sufficiently to enable it to be removed from the replicative surface securely attached to the sheet material and with the replicated surface effect in the coating being maintained; and
E. means for stripping the sheet material from the replicative surface with the at least partially set coating adhered to the sheet material, characterized by the replicative surface comprising a cylinder having the desired surface effect in the central portion of its outer cylindrical surface, said surface effect extending laterally less than the width of the sheet material on both sides and being bordered on both sides by cylindrical bands of a smooth surface extending beyond the width of the sheet material and having a diameter no less than the diameter of the valleys of the contoured surface effect area, whereby the set coating material can fill all of the desired surface effect area and extend laterally into the area of the smooth surface bands and can be stripped cleanly from the replicative surface and the smooth surface bands.

BEST MODE FOR CARRYING OUT THE INVENTION

Figure 1:
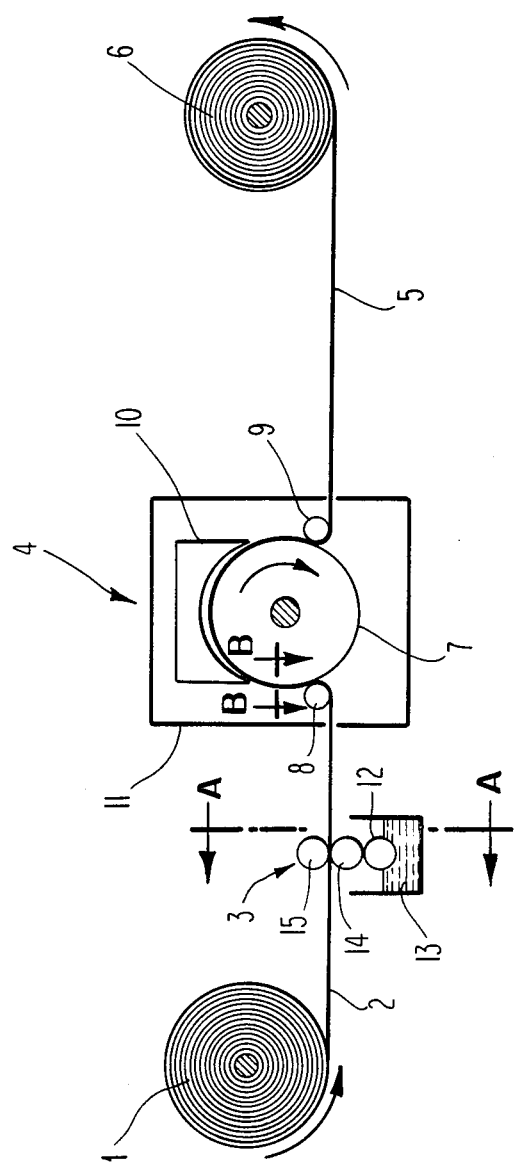
FIG. 1 of the drawings illustrates schematically the preferred apparatus for carrying out the present invention, wherein a base paper substrate is coated and pressed against a patterned replicating roll, after which the paper, coating and roll are revolved together past an electron beam curing station where the coating is cured, and then the paper, with the cured coating adhered to it, is stripped from the roll.

Referring to FIG. 1, a roll 1 of base paper 2 is unwound and passed through a coating station 3 and an electron beam curing station 4, after which the paper 5 having a cured coating thereon is wound onto roll 6.

The curing station 4 includes a patterned replicative roll 7, in which the desired texture is engraved or otherwise formed in the surface of the roll. The coated paper 2 is pressed against the replicating roll 7 by press roll 8 to assure that the coating fills the depressions in the textured surface of the replicating roll and that there is continuous intimate contact of the coating with the paper. The replicative roll 7 is mounted for rotation by conventional drive means (not shown) and continuously carries the paper and coating past an electron beam radiation unit 10 which irradiates the coating through the paper and cures it at least sufficiently to permit it to be removed from the replicative roll 7 at take-off roll 9, securely attached to the paper, and to assure permanent replication of the desired surface in the coating.

The amount of coating applied to the substrate can be varied somewhat, depending upon the surface effect and pattern depth on the replicative surface. Typically the coating thickness would be between about 25 and 75 micrometers. The coating is spread by the pressure of the press roll 8 and fills the contours of the replicative surface while providing a continuous layer on the substrate. The amount of coating will typically range from about 22.2 grams to about 44.4 grams per square meter (15–30 lbs. per ream of 3300 square feet).

If the replication pattern contours are to be reproduced in the coating only and not also in the paper substrate, the coating must be sufficiently thick to permit this. If the pattern contours are to be reproduced in the paper also, less coating can be used and higher pressure and a harder press roll 8 would be used.

Electron beam radiation units useful in the present invention are readily available and typically consist of a transformer capable of stepping up line voltage and an electron accelerator. In one type of machine the electrons are generated from a point source filament and then scanned electromagnetically like a television set to traverse the coated object. In another type of machine, the electrons are generated in a curtain from an extended filament which can irradiate the entire width of the surface without the need for scanning. While commercial machines are available with accelerating voltages of over a million electron volts, the range for this and similar coating applications is typically from 150–300 KV (kiloelectron volts). The entire curing station 4 is enclosed in a lead lined enclosure 11 to prevent stray radiation from leaving the curing station area. It is common when curing coatings with electron beam radiation units to take steps to eliminate oxygen from the surface of the coating. In the present apparatus, a nitrogen atmosphere can be applied.

The coating applied to the paper in the preferred embodiment must be capable of being cured by electron beam radiation. Typical resins useful in electron beam curable coatings are stryrenated polyesters and acrylics, such as vinyl copolymers of various monomers and glycidyl methacrylate reacted with acrylic acid, isocyanate prepolymers reacted with an hydroxyalkyl acrylate, epoxy resins reacted with acrylic or methacrylic acid, and hydroxyalkyl acrylate reacted with an anhydride and subsequently reacted with an epoxy. In some cases it may be desirable to include small amounts of conventional release agents, such as silicone oils.

Coating compositions which can be cured by electron beam radiation and are suitable for release functions generally include some or all of the following:
(a) a moderate molecular weight (300 to 800 g./mole) functional oligomer;
(b) a reactive monomer diluent (a mono or multifunctional acrylate or methacrylate) such as trimethylolpropane triacrylate or isodecyl acrylate;
(c) pigments or fillers such as clay, silica or diatomaceous earth;
(d) reactive or nonreactive silicones; and
(e) organic diluents such as acetone or carbon tetrachloride.

Figure 2:
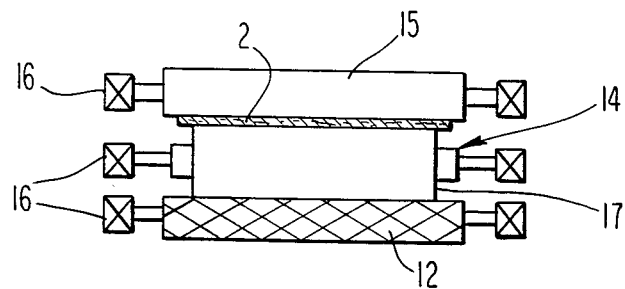
FIG. 2 illustrates the apparatus for coating the paper.

The coating station 3 is further illustrated in FIG. 2, which is an elevation view taken along lines A—A in FIG. 1. Referring to FIGS. 1 and 2, coating station 3 is provided by a conventional engraved coating pick-up roll 12 rotating through a reservoir 13 of coating material and a coating transfer roll 14 forming a nip with backing roll 15, through which the paper 2 passes. All of the coating station rolls 12, 14 and 15 are mounted for rotation in bearings 16 and driven by conventional means (not shown). The coating pick-up roll 12 picks up a predetermined layer of coating material and transfers it to coating transfer roll 14, which in turn transfers the coating to one side of paper 2.

Coating transfer roll 14 includes a raised cylindrical surface 17 which extends less than the width of paper 2 on both sides of the paper. Only the raised surface 17 transfers coating to the paper 2, and therefore a band along each edge of the paper is uncoated. This is important because coating to the very edge of the paper would make it impossible to avoid the coating being squeezed upon the replication roll beyond the paper where it would not be removed after curing. The raised surface 17 typically has a diameter about 1 centimeter greater than the rest of the transfer roll 14.

Coating pick-up roll 12 and backing roll 15 are typically manufactured from steel and are preferably chrome plated. Transfer roll 14 is preferably manufactured from a hard rubber material. The width of the backing roll 15 is at least as wide, and preferably wider than the paper 2. The width of the pick-up roll 12 is at least as wide and preferably wider than the raised surface 17 of the transfer roll 14.

Figure 3:
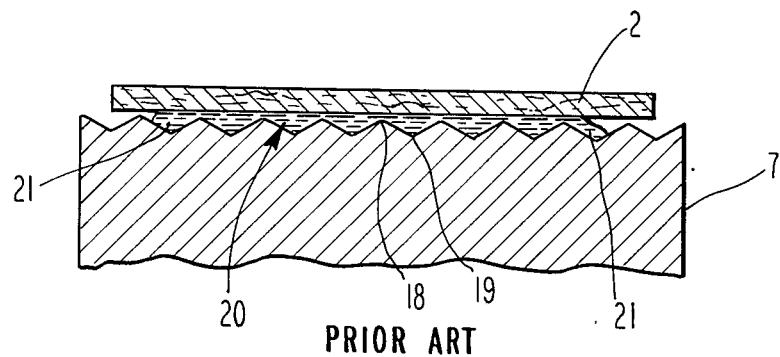
FIG. 3 illustrates the prior art replicating roll.
Figure 4:
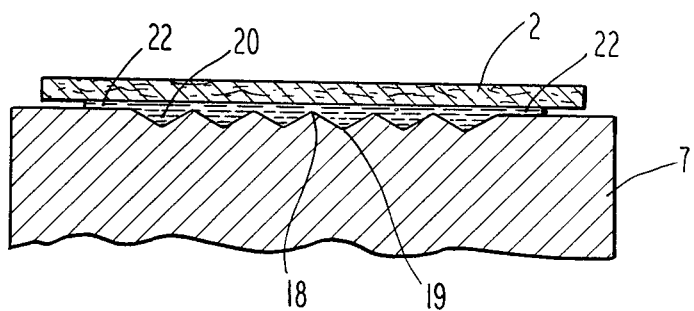
FIG. 4 illustrates the improved replicating roll of the invention.

FIGS. 3 and 4 illustrate partial cutaway views of the paper 2 and replicative roll 7 taken along lines B—B of FIG. 1. FIG. 3 illustrates the prior art replicative roll 7, wherein the replication pattern, illustrated by peaks 18 and valleys 19, extends beyond the edges of the paper 2. As can be seen in this embodiment, the coating 20 is squeezed laterally along the paper and only partially fills the edge cells at 21 as its thickness diminishes at the edges. This partial filling reduces or eliminates the adherence of the coating to the paper at the edges, and the coating remains in the edge cells after removal of the paper. As already described, more and more of the coating builds up at this edge until the equipment must be shut down for cleaning.

FIG. 4 illustrates the replicative roll 7 of the invention, where smooth surface cylindrical bands border the contoured pattern formed by peaks 18 and valleys 19 and are positioned so that the coating 20 extends into the bands to form uniformly thick layers 22 in intimate contact with the paper 2. The smooth surface bands must have a diameter which is at least as great as the minor diameter of the contoured pattern (valleys 19). Preferably, the smooth surface bands have a diameter which is at least as great as the major diameter of the contoured pattern (peaks 18), which means that all of the pattern is equal to or below the diameter of the roll measured at the smooth surface bands.

Thus, when a freshly coated web is pressed against the roll, excess coating between the web and the roll is evenly spread out onto the smooth surface bands, providing a minimum coating film thickness and one which readily separates intact from the roll on the paper web.

One method for fabricating the replicative roll 7 of the invention is to start with the engraved roll of the prior art (FIG. 3) and grind or turn down the ends to a smaller diameter. Then smooth cylindrical ring sleeves are pressed onto the ends of the roll 7. After thay they are polished to the desired smoothness. By way of example only, the smoothness of the bands of a satisfactory roll of the invention was measured to have an arithmatic average (of amplitudes of a needle traveling over the surface being measured) of 0.16 micrometers (with a 0.030 micrometer cut off). However, the degree of smoothness is not narrowly critical, it only being necessary to provide smoothness which is typically obtained from grinding and polishing or other finishing operations.

A preferred method for fabricating the replicative roll 7 is to start with a smooth surface cylinder and engrave the contoured pattern in the central portion of the roll, leaving the ends smooth and at the same diameter as the maximum diameter (peaks 18) of the contoured pattern. The smooth surface bands on the ends can then be ground or turned down further, if desired, but not below the valleys 19 of the contoured pattern.

By way of example, a replicative roll fabricated by the preferred method had the smooth surface bands and one inch of each end of the contoured pattern ground down until the pattern was just barely removed. Thus, the diameter of the smooth surface bands was the same as the minimum (valleys 19) of the contoured surface effect area. The circumference of the maximum diameter of the contoured surface effect area was measured to have an average diameter of 9.254 inches. The circumferences of the smooth surface bands were measured to have an average diameter of 9.246 inches.

The apparatus was operated in the manner described for FIGS. 1 and 2 and resulted in all coating stripping cleanly with the paper. However, it would have been acceptable, although not preferred, for a small layer of the coating to stick on the smooth surface bands upon initial startup, as long as there was no continued buildup of the coating on the smooth surface bands. Thus, "stripping cleanly" can mean that all of the coating applied to the paper remains with the paper after initial startup, and clean shiny metal on the smooth surface bands is not always necessary. In the example just described, no coating remained on the smooth surface bands initially or later.

What is claimed is:

1. A method of providing surface replication in a coating on a sheet material, comprising the steps of:
   A. applying a flowable coating of a settable composition or material to one side of a web of sheet material;
   B. pressing the coated side of the sheet material against a replicative surface having a desired contoured surface effect having peaks and valleys to cause the surface of the coating to conform to the replicative surface;
   C. setting the coating to a nonflowable state at least sufficiently to enable it to be removed from the replicative surface securely attached to the sheet material and with the replicated surface effect in the coating being maintained; and
   D. stripping the sheet material from the replicative surface with the at least partially set coating adhered to the sheet material, characterized by the replicative surface comprising a cylinder having the desired surface effect in the central portion of its outer cylindrical surface, said surface effect extending laterally less than the width of the sheet material on both sides and being bordered on both sides by cylindrical bands of a smooth surface extending beyond the width of the sheet material and having a diameter no less than the diameter of the valleys of the contoured surface effect area, and the coating extending laterally into the area of the smooth surface bands, whereby the set coating material fills all of the desired surface effect area and is stripped cleanly from the replicative surface and the smooth surface bands.

2. The method according to claim 1, wherein the coating composition or material is electron beam curable and the coating is set in step C by curing with electron beam radiation.

3. The method according to claim 1, wherein the coating applied to the sheet material does not extend to the edge of either side of the sheet material.

4. The method according to claim 1, wherein the diameter of the smooth surface bands is at least as large as the maximum diameter of the desired surface effect area.

5. The method according to claim 1, wherein the diameter of the smooth surface bands is the same as the maximum (peaks') diameter of the desired surface effect area.

6. An apparatus for providing surface replication in a settable coating on a sheet material, comprising:
   A. a replicative surface having a desired contoured surface effect of peaks and valleys and being provided by a cylindrical surface mounted for revolution;
   B. coating means for applying a coating of a settable composition or material directly to one side and short of either edge of the sheet material;
   C. pressing means for pressing the coated side of the sheet material against the replicative surface to cause the surface of the coating opposite the sheet material to conform to the replicative surface.
   D. means for setting the coating to a nonflowable state at least sufficiently to enable it to be removed from the replicative surface securely attached to the sheet material and with the replicated surface effect in the coating being maintained; and
   E. means for stripping the sheet material from the replicative surface with the at least partially cured coating adhered to the sheet material, characterized by the replicative surface comprising a cylinder having the desired surface effect in the central portion of its outer cylindrical surface, said surface effect extending laterally less than the width of the sheet material on both sides and being bordered on both sides by cylindrical bands of a smooth surface extending beyond the width of the sheet material and having a diameter no less than the diameter of the valleys of the contoured surface effect area, whereby the set coating material can fill all of the desired surface effect area and extend laterally into the area of the smooth surface bands and can be stripped cleanly from the replicative surface and the smooth surface bands.

7. The apparatus according to claim 6, wherein the replicative surface is provided by a drum and said smooth surface bands are provided by cylindrical rings installed on the ends of the drum.

8. The apparatus according to claim 6, wherein the diameter of the smooth surface bands is at least as large as the maximum diameter of the desired surface effect area.

9. The apparatus according to claim 6, wherein the diameter of the smooth surface bands is the same as the maximum (peaks') diameter of the desired surface effect area.

* * * * *